(12) United States Patent
Ingle et al.

(10) Patent No.: US 7,575,595 B2
(45) Date of Patent: Aug. 18, 2009

(54) ANNULOPLASTY RING AND HOLDER COMBINATION

(75) Inventors: Aaron S. Ingle, Costa Mesa, CA (US); Hilda Zhang Fann, Fountain Valley, CA (US); W. Vaso Adzich, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 102 days.

(21) Appl. No.: 11/386,429

(22) Filed: Mar. 22, 2006

(65) Prior Publication Data

US 2006/0217803 A1    Sep. 28, 2006

Related U.S. Application Data

(60) Provisional application No. 60/664,875, filed on Mar. 23, 2005.

(51) Int. Cl.
*A61F 2/24* (2006.01)
(52) U.S. Cl. ..................................... 623/2.36
(58) Field of Classification Search ............... 623/2.11, 623/2.36
See application file for complete search history.

(56) References Cited

U.S. PATENT DOCUMENTS

| | | | |
|---|---|---|---|
| 3,656,185 A | 4/1972 | Carpentier | |
| 3,828,787 A | 8/1974 | Anderson et al. | |
| 4,042,979 A | 8/1977 | Angell | |
| 4,055,861 A | 11/1977 | Carpentier et al. | |
| 4,106,129 A | 8/1978 | Carpentier et al. | |
| 4,164,046 A | 8/1979 | Cooley | |
| 4,185,636 A | 1/1980 | Gabbay et al. | |
| 4,217,665 A | 8/1980 | Bex et al. | |
| 4,364,126 A | 12/1982 | Rosen et al. | |
| 4,489,446 A | 12/1984 | Reed | |
| 4,492,229 A | 1/1985 | Grunwald | |
| 4,506,394 A | 3/1985 | Bedard | |
| 4,535,483 A | 8/1985 | Klawitter | |
| 4,585,453 A | 4/1986 | Martin et al. | |
| 4,602,911 A | 7/1986 | Ahmadi et al. | |

(Continued)

FOREIGN PATENT DOCUMENTS

EP    0 338 994    10/1989

(Continued)

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

(Continued)

*Primary Examiner*—Bruce E Snow
(74) *Attorney, Agent, or Firm*—Rajiv Yadav; Guy Cumberbatch (57) ABSTRACT

An annuloplasty ring holder includes an angled post for improved visibility and access by the surgeon. The post may be configured to be adjusted in angle and rotation. The ring holder can include a relatively open lower template, including relatively narrow extending radial arms with short, generally arcuate ring-retaining distal portions. The invention includes placements of suture holes and cutting wells which, in combination with improved suture routing, afford the user improved access to cutting the suture that is used to retain the annuloplasty ring to the holder.

9 Claims, 10 Drawing Sheets

U.S. PATENT DOCUMENTS

| | | | |
|---|---|---|---|
| 4,612,011 A | 9/1986 | Kautzky | |
| 4,655,218 A | 4/1987 | Kulik et al. | |
| 4,679,556 A | 7/1987 | Lubock et al. | |
| 4,683,883 A | 8/1987 | Martin | |
| 4,702,250 A | 10/1987 | Ovil et al. | |
| 4,743,253 A | 5/1988 | Magladry | |
| 4,750,492 A | 6/1988 | Jacobs | |
| 4,755,181 A | 7/1988 | Igoe | |
| 4,759,758 A | 7/1988 | Gabbay | |
| 4,865,600 A | 9/1989 | Carpentier et al. | |
| 4,911,164 A | 3/1990 | Roth | |
| 4,932,965 A | 6/1990 | Phillips | |
| 5,011,481 A | 4/1991 | Myers et al. | |
| 5,041,130 A | 8/1991 | Cosgrove et al. | |
| 5,061,277 A | 10/1991 | Carpentier et al. | |
| 5,064,431 A | 11/1991 | Gilbertson et al. | |
| 5,104,407 A * | 4/1992 | Lam et al. | 623/2.36 |
| 5,201,880 A | 4/1993 | Wright et al. | |
| 5,258,021 A | 11/1993 | Duran | |
| 5,290,300 A | 3/1994 | Cosgrove et al. | |
| 5,306,296 A | 4/1994 | Wright et al. | |
| 5,350,420 A | 9/1994 | Cosgrove et al. | |
| 5,415,667 A | 5/1995 | Frater | |
| 5,496,336 A | 3/1996 | Cosgrove et al. | |
| 5,593,435 A | 1/1997 | Carpentier et al. | |
| 5,607,471 A | 3/1997 | Seguin et al. | |
| 5,669,919 A | 9/1997 | Sanders et al. | |
| 5,674,279 A | 10/1997 | Wright et al. | |
| 5,683,402 A | 11/1997 | Cosgrove et al. | |
| 5,776,189 A | 7/1998 | Khalid | |
| 5,824,066 A | 10/1998 | Gross | |
| 5,824,069 A | 10/1998 | Lemole | |
| 5,888,240 A | 3/1999 | Carpentier et al. | |
| 5,972,030 A | 10/1999 | Garrison et al. | |
| 6,019,739 A | 2/2000 | Rhee et al. | |
| 6,024,918 A | 2/2000 | Hendriks et al. | |
| 6,102,945 A | 8/2000 | Campbell | |
| 6,143,024 A | 11/2000 | Campbell et al. | |
| 6,159,240 A | 12/2000 | Sparer et al. | |
| 6,183,512 B1 | 2/2001 | Howanec, Jr. et al. | |
| 6,187,040 B1 | 2/2001 | Wright | |
| 6,217,610 B1 | 4/2001 | Carpentier et al. | |
| 6,231,602 B1 | 5/2001 | Carpentier et al. | |
| 6,250,308 B1 | 6/2001 | Cox | |
| 6,258,122 B1 | 7/2001 | Tweden et al. | |
| 6,283,993 B1 | 9/2001 | Cosgrove et al. | |
| 6,319,280 B1 | 11/2001 | Schoon | |
| 6,391,054 B2 | 5/2002 | Carpentier et al. | |
| 6,406,492 B1 | 6/2002 | Lytle | |
| 6,406,493 B1 | 6/2002 | Tu et al. | |
| 6,419,696 B1 | 7/2002 | Ortiz et al. | |
| 6,602,288 B1 | 8/2003 | Cosgrove et al. | |
| 6,602,289 B1 | 8/2003 | Colvin et al. | |
| 6,619,291 B2 | 9/2003 | Hlavka et al. | |
| 6,709,456 B2 | 3/2004 | Langberg et al. | |
| 6,718,985 B2 | 4/2004 | Hlavka et al. | |
| 6,719,786 B2 | 4/2004 | Ryan et al. | |
| 6,726,717 B2 | 4/2004 | Alfeiri et al. | |
| 6,749,630 B2 | 6/2004 | McCarthy et al. | |
| 6,797,002 B2 | 9/2004 | Spence et al. | |
| 6,800,090 B2 | 10/2004 | Alferness et al. | |
| 6,802,860 B2 | 10/2004 | Cosgrove et al. | |
| 6,805,710 B2 | 10/2004 | Bolling et al. | |
| 6,858,039 B2 | 2/2005 | McCarthy | |
| 6,908,482 B2 | 6/2005 | McCarthy et al. | |
| 6,918,917 B1 | 7/2005 | Nguyen et al. | |
| 6,921,407 B2 | 7/2005 | Nguyen et al. | |
| 6,942,694 B2 | 9/2005 | Liddicoat et al. | |
| 6,955,689 B2 | 10/2005 | Ryan et al. | |
| 6,966,924 B2 | 11/2005 | Holmberg | |
| 6,986,775 B2 | 1/2006 | Morales et al. | |
| 7,037,334 B1 | 5/2006 | Hlavka et al. | |
| 7,066,954 B2 | 6/2006 | Ryan et al. | |
| 7,118,595 B2 | 10/2006 | Ryan et al. | |
| 7,125,421 B2 | 10/2006 | Tremulis et al. | |
| 7,166,126 B2 | 1/2007 | Spence et al. | |
| 7,166,127 B2 | 1/2007 | Spence et al. | |
| 7,294,148 B2 | 11/2007 | McCarthy | |
| 7,329,280 B2 | 2/2008 | Bolling et al. | |
| 2001/0034551 A1 | 10/2001 | Cox | |
| 2001/0049558 A1 * | 12/2001 | Liddicoat et al. | 623/2.36 |
| 2002/0129820 A1 | 9/2002 | Ryan et al. | |
| 2002/0133180 A1 | 9/2002 | Ryan et al. | |
| 2002/0169503 A1 | 11/2002 | Lytle | |
| 2002/0169504 A1 | 11/2002 | Alferness et al. | |
| 2002/0173844 A1 | 11/2002 | Alfieri et al. | |
| 2003/0033009 A1 | 2/2003 | Gabbay | |
| 2003/0040793 A1 | 2/2003 | Marquez | |
| 2003/0045929 A1 * | 3/2003 | McCarthy et al. | 623/2.37 |
| 2003/0083742 A1 | 5/2003 | Spence et al. | |
| 2003/0093148 A1 | 5/2003 | Bolling et al. | |
| 2003/0125715 A1 * | 7/2003 | Kuehn et al. | 606/1 |
| 2004/0006384 A1 | 1/2004 | McCarthy | |
| 2004/0249452 A1 | 12/2004 | Adams et al. | |
| 2004/0249453 A1 | 12/2004 | Cartledge et al. | |
| 2005/0004666 A1 | 1/2005 | Alfieri | |
| 2005/0043791 A1 | 2/2005 | McCarthy et al. | |
| 2005/0131533 A1 | 6/2005 | Alfieri et al. | |
| 2005/0182487 A1 | 8/2005 | McCarthy et al. | |
| 2005/0192666 A1 | 9/2005 | McCarthy | |
| 2005/0197696 A1 | 9/2005 | Gomez Duran | |
| 2005/0246014 A1 | 11/2005 | McCarthy | |
| 2005/0256567 A1 | 11/2005 | Lim et al. | |
| 2005/0256568 A1 | 11/2005 | Lim et al. | |
| 2005/0256569 A1 | 11/2005 | Lim et al. | |
| 2005/0267572 A1 | 12/2005 | Schoon et al. | |
| 2005/0278022 A1 | 12/2005 | Lim | |
| 2005/0288776 A1 | 12/2005 | Shaoulian et al. | |
| 2005/0288777 A1 | 12/2005 | Rhee et al. | |
| 2005/0288778 A1 | 12/2005 | Shaoulian et al. | |
| 2005/0288780 A1 | 12/2005 | Rhee et al. | |
| 2005/0288782 A1 | 12/2005 | Moaddeb et al. | |
| 2005/0288783 A1 | 12/2005 | Shaoulian et al. | |
| 2006/0015178 A1 | 1/2006 | Moaddeb et al. | |
| 2006/0015179 A1 | 1/2006 | Bulman-Fleming et al. | |
| 2006/0020336 A1 | 1/2006 | Liddicoat | |
| 2006/0025856 A1 | 2/2006 | Ryan et al. | |
| 2006/0025858 A1 | 2/2006 | Alameddine | |
| 2006/0030885 A1 | 2/2006 | Hyde | |

FOREIGN PATENT DOCUMENTS

| | | |
|---|---|---|
| EP | 0 595 791 | 5/1994 |
| EP | 0 860 151 | 8/1998 |
| EP | 1 034 753 | 9/2000 |
| FR | 2 708 458 | 8/1993 |
| WO | WO 95/03757 | 2/1995 |
| WO | WO 01/19292 | 3/2001 |
| WO | WO 01/26586 | 4/2001 |
| WO | WO 01/47438 | 7/2001 |
| WO | WO 01/87191 | 11/2001 |
| WO | WO 02/03892 | 1/2002 |
| WO | WO 03/020178 | 3/2003 |
| WO | WO 03/041617 | 5/2003 |
| WO | WO 2004/004607 | 1/2004 |
| WO | WO 2005/034813 | 4/2005 |
| WO | WO 2005/110290 | 11/2005 |
| WO | WO 2007/050506 | 5/2007 |

OTHER PUBLICATIONS

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Cochran, et al., Effect of Papillary Muscle Position on Mitral Valve Function: Relationship to Homografts, The Society of Thoracic Surgeons, pp. 5155-5161, 1998.

D.C. Miller, IMR Redux- To Repair or Replace?, Journal of Thoracic & Cardiovascular Surgery, pp. 1-8, 2001.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

PCT International Search Report (PCT/US2004/032596) Mailed Jun. 20, 2005.

PCT International Search Report (PCT/US2005/014585) Mailed Sep. 29, 2005.

PCT International Search Report (PCT/US2005/020583) Mailed Oct. 11, 2005.

PCT International Search Report (PCT/US2006/001405) Mailed Jan. 13, 2006.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Techniques for 3D Quantitative Echocardiography, University of Washington Cardiovascular Research & Training Center Cardiac Imaging Research Lab, pp. 1-5, Oct. 2003.

* cited by examiner

ANNULOPLASTY RING AND HOLDER COMBINATION

RELATED APPLICATIONS

This application claims priority from U.S. Provisional Application Ser. No. 60/664,875, filed on Mar. 23, 2005, the contents of which are expressly incorporated herein in their entirety.

FIELD OF THE INVENTION

The present invention relates generally to medical devices, and particularly to repair of heart valves using annuloplasty rings.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid, and pulmonary, and are each mounted in an annulus comprising dense fibrous rings attached either directly or indirectly to the atrial and ventricular muscle fibers.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Valve disease involving the mitral valve often involves secondary mitral regurgitation (MR), a complication of end-stage cardiomyopathy which is the backflow of blood from the left ventricle (LV) to the left atrium (LA) resulting from imperfections in the mitral valve. When the mitral valve allows blood to flow backward into the left atrium, the left ventricle must pump progressively harder to circulate blood throughout the body, which in turn promotes congestive heart failure (CHF).

Various surgical techniques may be used to repair a diseased or damaged valve. One method for treating defective valves is through repair or reconstruction. One repair technique that has been shown to be effective in treating incompetence is annuloplasty, in which the effective size and/or shape of the valve annulus is modified by securing a repair segment, such as an annuloplasty ring, around the heart valve annulus. For example, the valve annulus may be contracted by attaching a prosthetic annuloplasty repair segment or ring to an interior wall of the heart around the valve annulus. The annuloplasty ring is designed to support the functional changes that occur during the cardiac cycle: maintaining coaptation and valve integrity to prevent reverse flow while permitting good hemodynamics during forward flow.

The annuloplasty ring typically comprises an inner substrate, often formed from a metal (such as stainless steel or titanium) or from a flexible material (such as silicone rubber or Dacron cordage), which is typically covered with a biocompatible fabric or cloth to allow the ring to be sutured to the heart tissue. Depending on a particular application, annuloplasty rings may be stiff or flexible, may be split or continuous, and may have a variety of shapes, including circular, D-shaped, C-shaped, saddle-shaped, and/or kidney-shaped. Examples are seen in U.S. Pat. Nos. 5,041,130, 5,104,407, 5,201,880, 5,258,021, 5,607,471, 6,187,040, and 6,805,710, the contents of which are incorporated herein by reference in their entirety. Many annuloplasty rings are formed in a plane, but some rings are generally non-planar. Such non-planar rings can be saddle-shaped, and/or bowed along various portions, such as being bowed along their anterior or straight side to conform to the desired shape of the annulus at that location.

Implanting of annuloplasty rings can be a difficult procedure. Currently-available methods include open-heart surgery and so-called minimally-invasive procedures. One particular difficulty is firmly holding the ring during the surgery. It is possible to implant rings by clamping the ring with forceps and/or the surgeon's fingers, but in many circumstances a specifically tailored annuloplasty ring holder is desirable. Examples of annuloplasty ring holders are depicted in U.S. Pat. Nos. 5,350,420; 5,683,402; and 6,749,630, the contents of which are incorporated herein by reference in their entirety.

Using a standard atriotomy approach to the mitral valve for repair, the surgeon does not generally achieve straight-on access to the mitral valve annulus. Instead, the surgeon often sees and accesses the valve from an angle. Therefore, when the sutures are placed in the annuloplasty ring and it is "parachuted" down to the annulus, the ring and holder must be reoriented to sit flat against the annulus. In minimally-invasive (MIS) approaches to the mitral valve, the annuloplasty ring must be passed through a relatively small port into the chest. This can be complicated by the bulk of some holders, so in some instances a surgeon simply removes the holder from the ring prior to "parachuting" the ring down the sutures and onto the valve annulus. However, the removal of the entire holder from the ring can make control of the annuloplasty ring more difficult.

Another issue is visibility of the ring and valve annulus during the implantation procedure. Some holders block significant portions of the surgeon's view, which can make the surgical procedure more difficult. To enhance visibility, some holders make use of transparent and/or translucent materials. Some holders use a so-called "window" approach, wherein openings are positioned in the template portion of the holder. The openings serve as windows in the holder template through which the user can view the surgical procedure. Examples of such holders are described in U.S. Pat. Nos. 5,683,402 and 6,749,630, the contents of which are incorporated by reference herein in their entirety.

Another issue is securing the ring to the holder in a releasable but secure manner. Many holders use multiple retaining sutures to secure a ring to the holder. In order to release the ring from the holder, the user severs the retaining sutures. Increasing the number of sutures can cause the ring to be more securely held to the holder, but can increase the steps necessary for the surgeon to release the ring from the holder. Additionally, the positioning of the retaining sutures is important in that the user must be able to access and sever the sutures to release the ring from the holder. Many prior ring holders made use of suture wells located at various positions about the holder, with the location of such wells corresponding to locations about the ring including the posterior and anterior portions of the ring. During implantation procedures, some of these locations may be difficult for a surgeon to access in order to sever the suture.

Accordingly, there has been a need for an improved apparatus, system, and method to implant an annuloplasty ring. The present invention satisfies one or more of these needs.

SUMMARY OF THE INVENTION

The present application is generally described with respect to its use in the repair of the mitral valve, which regulates blood flow from the left atrium (LA) to the left ventricle (LV). However, the invention could also be applied to repair of other valves, such as the tricuspid or aortic valve repairs.

The invention includes three main features for annuloplasty ring holder technology. The first feature is the application of reduced structural elements on the holder, including arms and/or knobs, to increase the visibility for the user during the implantation procedure.

The second feature is the use of an angled post, which is either fixed or adjustable. The angled post may also be rotationally adjustable about the longitudinal axis of the holder. The surgeon does not generally achieve direct straight-on access to the valve annulus, but instead typically sees and accesses the valve from an angle. By applying an angle to the post with respect to the plane of the annulus, a more intuitive orientation of the ring, and parachuting of the ring down onto the valve annulus, can be achieved.

The third feature is the improved placement of suture wells, and improved suturing techniques that facilitate severing the suture lines and assembly of the device. The invention used one or more suture wells that are positioned so as to enhance visibility and accessibility of the suture wells to the surgeon or other user. Moreover, the suture routing provides wider attachment points for greater stability of the ring on the holder.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIGS. 2A-2C are various views of the annuloplasty ring from FIG. 1;

FIGS. 3A-3F are various views of the ring holder from FIG. 1;

DETAILED DESCRIPTION OF THE INVENTION

Figure 1:
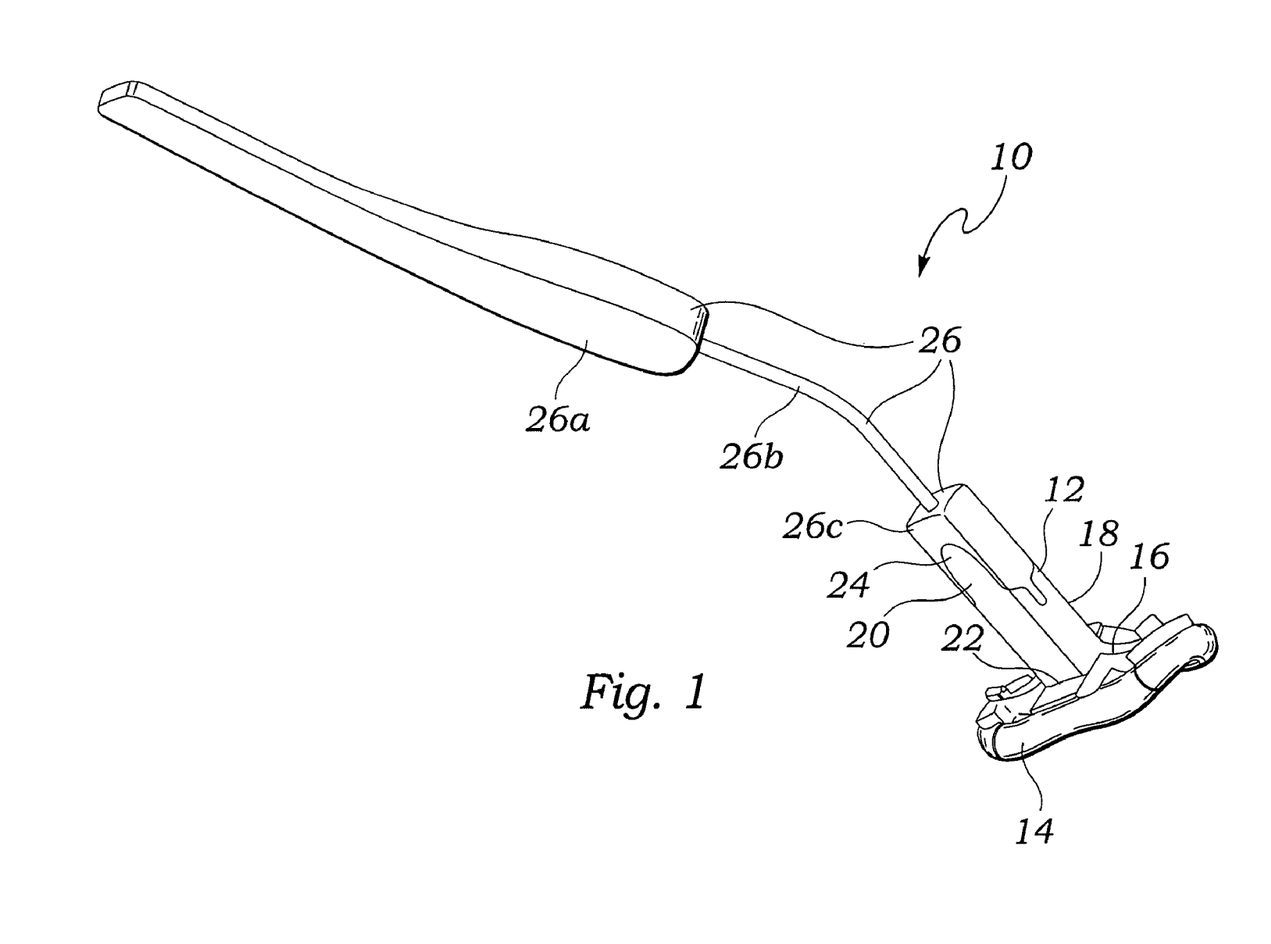
FIG. 1 depicts a perspective view of an assembly having a ring, ring holder, and handle according to an embodiment of the invention.

One embodiment of the invention is depicted in FIG. 1. The device 10 comprises a holder 12 and annuloplasty ring 14. The holder 12 has a lower template portion 16 secured to a post 18. In the embodiment depicted, the post 18 has a proximal end 20 and distal end 22, with the distal end 22 secured to the template portion 16. The post proximal end 20 includes an attachment assembly 24 by which a handle 26 can be removably secured to the post 18. The handle 26 includes a proximal portion 26a, a middle portion 26b, and a distal (attachment) portion 26c. The distal portion 26c is configured to cooperate with the attachment assembly 24 in order to secure the handle 26 to the post 18. The middle portion 26b of the handle may be malleable, thereby permitting a surgeon to adjust (via bending) the handle to a configuration convenient for the particular application and surgeon.

Figure 1A:
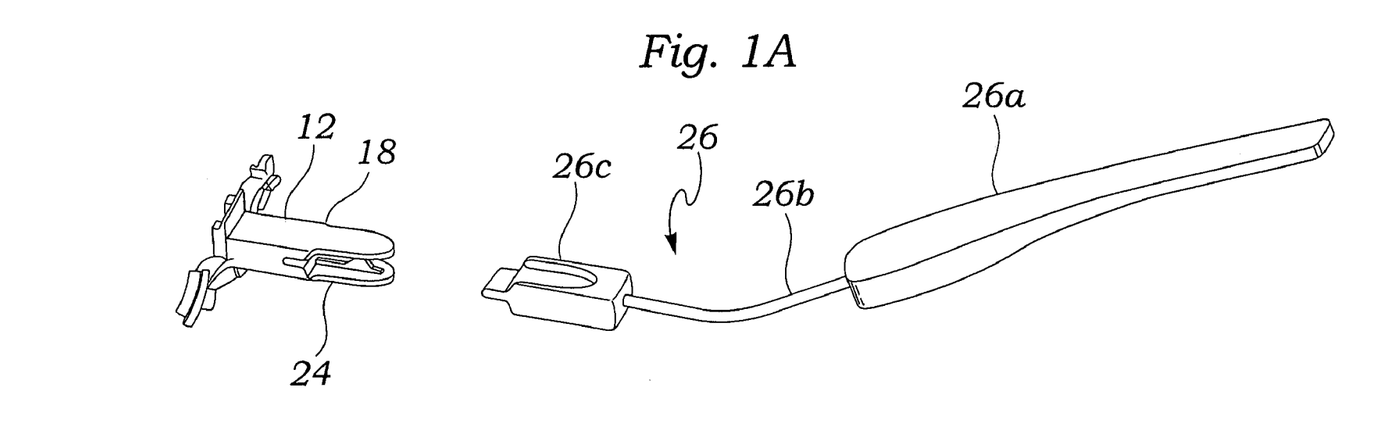
FIGS. 1A and 1B depict perspective views of an assembly having a ring holder and handle according to an embodiment of the invention.
Figure 1B:
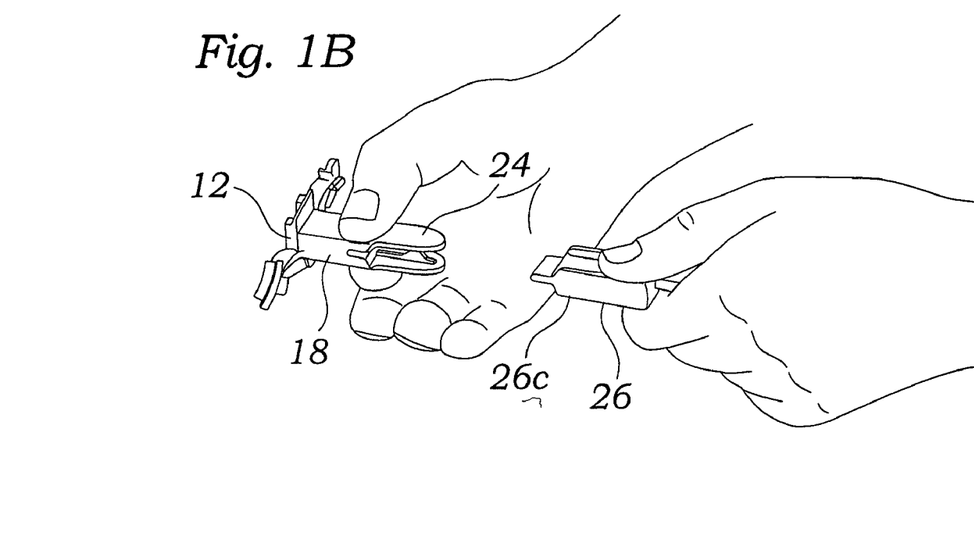

Attachment and removal of the handle 26 to and from the post 18 are depicted in FIGS. 1A and 1C. The handle 26 can be secured to the post 18 by snapping the handle distal portion 26c into the attachment assembly 24. Removing the handle 26 is accomplished by gripping the holder 12 while pulling the handle 26.

Figure 2A:
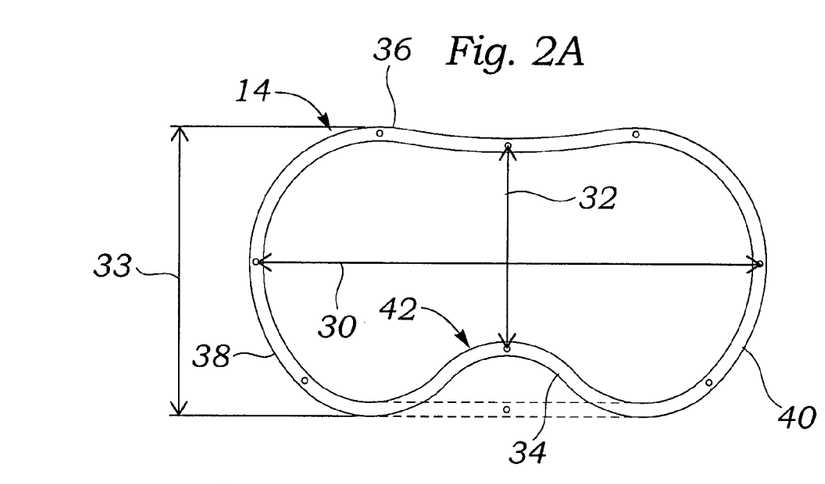
Figure 2B:
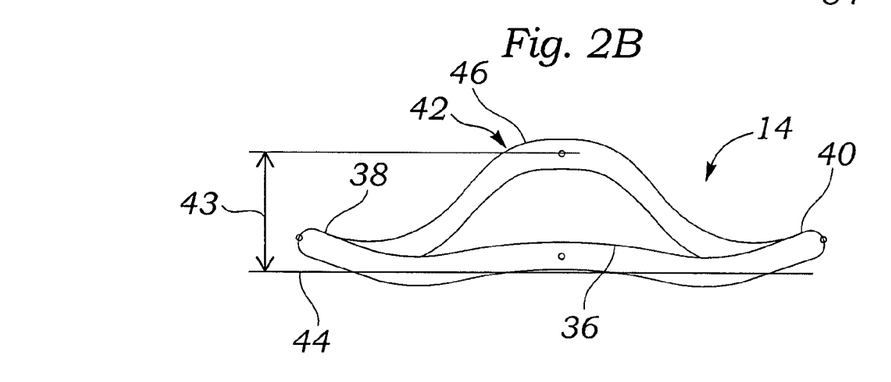
Figure 2C:
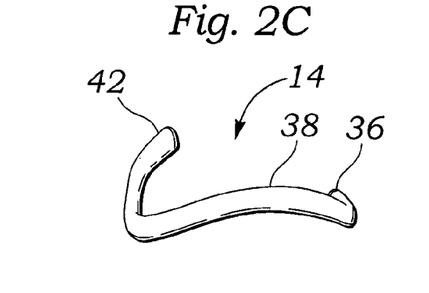
Figures 3A, 3C:
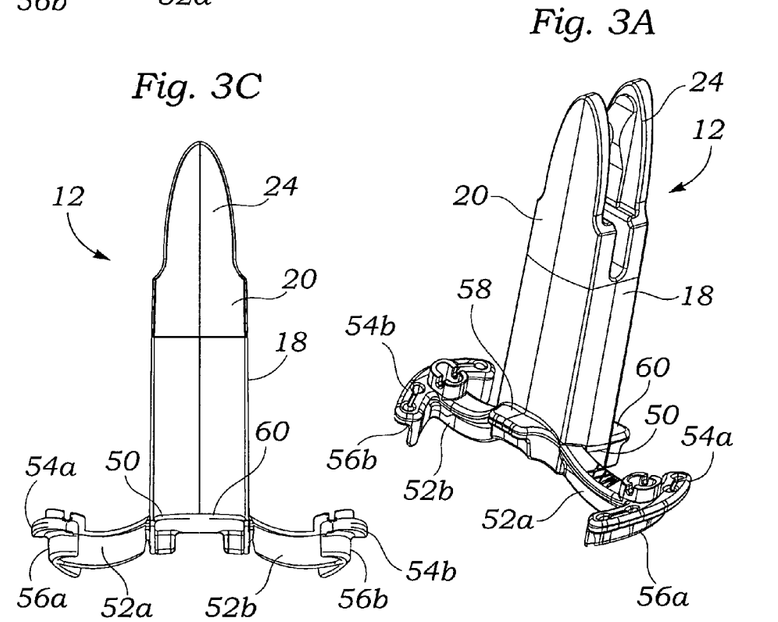
Figure 3B:
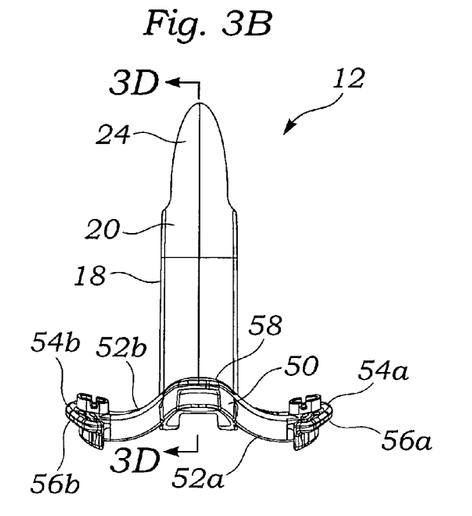
Figure 3D:
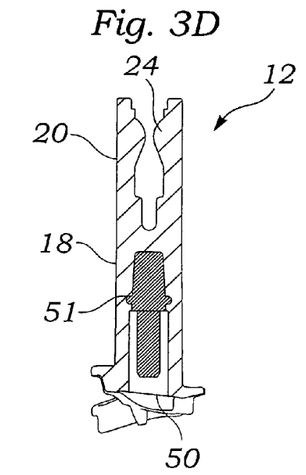
Figure 3E:
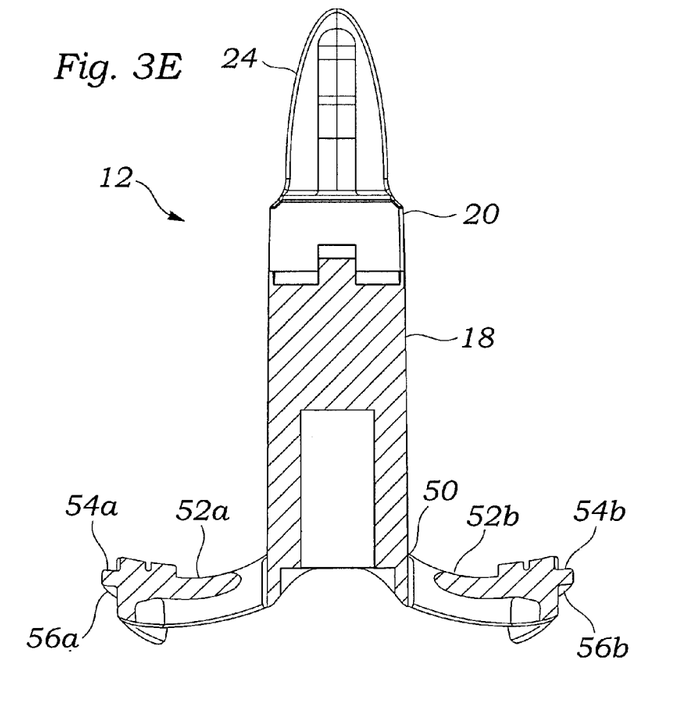
Figure 3F:
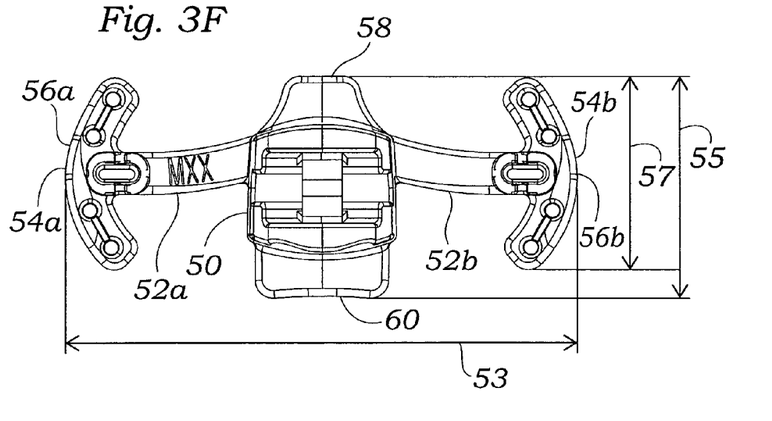

FIGS. 2A-2C are plan, front elevational, and side elevational views, respectively, of an annuloplasty ring 14 from FIG. 1. The ring 14 is generally oval-shaped about a major axis 30 and a minor axis 32, with a maximum height dimension 33 measured parallel to the minor axis 32. In the embodiment depicted, the ring major axis 30 is more than twice as long as the minor axis 32, and only slightly less than twice as long as the maximum height 33. The ring has a posterior portion 34, an anterior portion 36, and sides 38, 40. A mid-section 42 of the posterior portion 34 of the ring 14 bows upward and inward. The elevation 43 above a datum plane 44 is seen in FIG. 2B, while the magnitude of the inward bow of the mid-section 42 is seen in FIG. 2A. The sides 38, 40 also bow upward as indicated in FIG. 2B. Finally, the anterior portion 36 bows upward and inward. The mid-section 42 forms a plateau 46 in the Z-direction centered about the minor axis 32 as seen in FIG. 2B. The ring can be formed from various materials, such as stainless steel, titanium, Stellite, cloth, etc. The choice of materials and specific design of the ring depend on the particular application. In the embodiment of FIGS. 2A-2C, the ring 14 has a specific shape, including a major axis 30 that is approximately twice as long as the maximum height 33. However, the invention is not limited to rings where the maximum width (i.e., major axis) is substantially greater than the maximum height. Other shapes are also within the scope of the invention. Additionally, the ring may be relatively flexible or relatively stiff, or may be a combination of stiff and flexible portions.

FIG. 3A-3F depict the holder 12 from FIG. 1 in greater detail. The holder 12 includes a central base portion 50. First and second arms 52a, 52b extend from the central base portion 50. At the distal ends 54a, 54b of the first and second arms 52a, 52b are ring securing portions 56a, 56b against which one or more portions of an annuloplasty ring can be positioned. The holder 12 has a maximum width 53 and a maximum height 55. In the embodiment depicted, the securing portions 56a, 56b are generally arcuate segments which are configured to engage side portions 38, 40 of the annuloplasty ring depicted in FIGS. 2A-2C. In the embodiment of FIGS. 3A-3F, the generally arcuate segments are relatively short, having a height 57 less than the maximum height 55 of the holder 12. The length of each of the generally arcuate segments of the securing portions 56a, 56b (measured along the curved outer edge thereof that engages the ring inner edge) is also relatively small, and in the particular embodiment depicted is less than 50% of the maximum width 53 of the holder 12, is less than the maximum height 55 of the holder 12, is less than the length of the minor axis 32 of a ring that might be fastened to the holder 12 (as in FIG. 10A). Depending on the particular embodiment, the length of a generally arcuate segment of the securing portions 56a, 56b may even be less than the length of the corresponding radial arm 52a, 52b.

In the embodiment of FIGS. 3A-3F, a posterior knob portion 58 is configured to engage a posterior portion 34 of the annuloplasty ring 14, and an anterior knob portion 60 is configured to engage an anterior portion 36 of the annuloplasty ring 14. The knob portions 58, 60 provide additional support to the annuloplasty ring 14. Although the embodiment depicted in FIGS. 3A-3F has knob portions 58, 60 that lack any suture holes through which sutures can pass to secure the ring to the knob portions, such sutures and knob portion suture holes are within the scope of the invention.

The holder 18 can be formed from various materials, or combinations of different materials, depending on the particular application. In one embodiment, the holder 12 is formed from a clear polysulfone. The holder 12 may also include markers for visibility under surgical conditions, such as radiopaque markers. In the embodiment depicted in FIG. 3D, the holder 12 includes a radiopaque marker 61 imbedded within the post 18. Such a radiopaque marker can be formed of various materials, such as polyphenylsulfone with 14% radiopaque bismuth subcarbonate.

In the embodiment depicted in FIGS. 3A-3F, the only structure leading from the central base portion 50 out to the annuloplasty ring is the two arms 52a, 52b and the knob portions 58, 60. By limiting the size (when viewed by the user from above) of the structure within the area enclosed by the ring (i.e., the central base portion 50, the arms 52a, 52b, and the knob portions 58, 60), the visibility afforded the user during the surgical procedure is improved over products having greater mass within the area enclosed by the ring.

Figure 4:
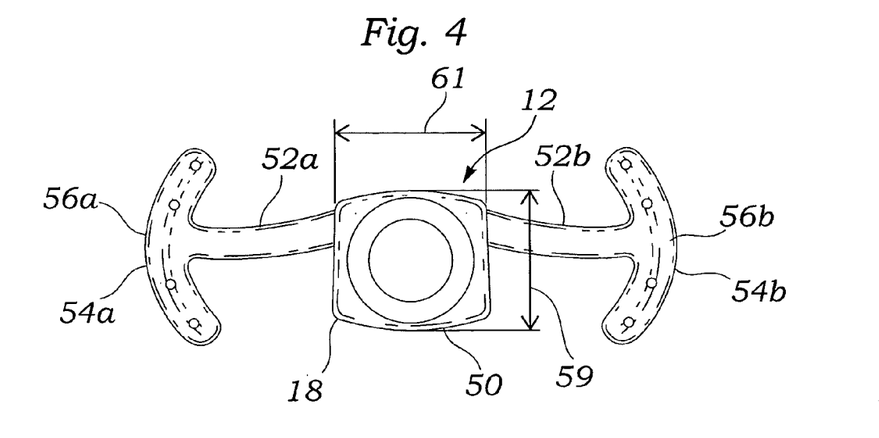
FIG. 4 is a top view of a ring holder according to an embodiment of the invention.
Figure 5:
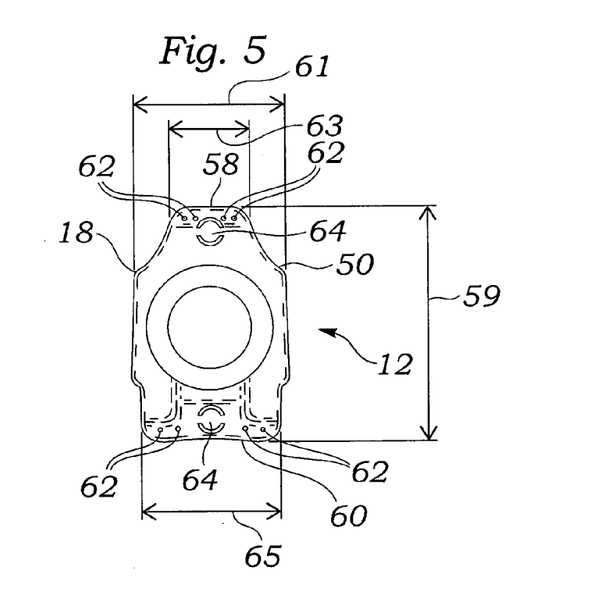
FIG. 5 is a top view of a ring holder according to an embodiment of the invention.

Depending on the particular application, including the type of ring being delivered and whether the ring rigid or flexible, one or both of the knobs 58, 60 and/or one or both of the arms 52a, 52b may be eliminated to further enhance the visibility. For example, in the embodiment depicted in FIG. 4, the knobs have been eliminated in favor of the arms 52a, 52b. The central base portion 50 has a maximum height 59 and maximum width 61. In the embodiment of FIG. 5, the arms have been eliminated in favor of the knobs 58, 60. The knobs 58, 60 each have suture holes 62 and corresponding cutting wells 64 through which sutures may pass to secure the ring to the knobs and holder. The knobs 58, 60 are narrower (in width) than the central base portion maximum width 61, and the knobs narrow toward their distal ends to distal widths 63, 65 less than the width 61 of the central base portion 50.

The central base portion 50 may also be further reduced in size, as may the knobs 58, 60 and arms 52a, 52b. The arms and/or knobs may also be relocated to different locations on the central base portion 50, depending on the particular application.

Figure 6:
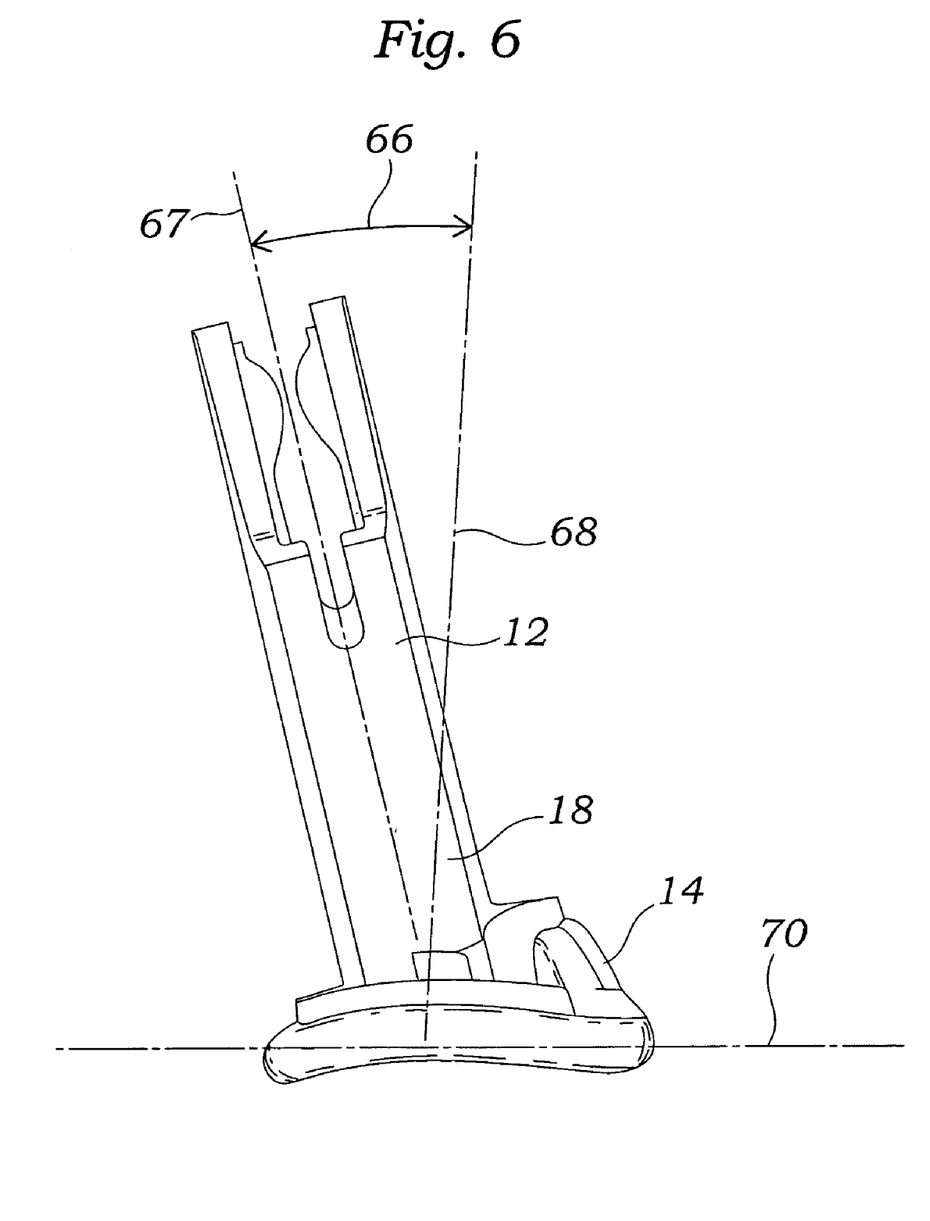
FIG. 6 is a side view of a ring holder according to an embodiment of the invention.

Another aspect of the invention is the positioning of the post with respect to the ring. By applying an appropriate angle to the post of the holder with respect to the ring, the plane of the ring will naturally be parallel to the plane of the annulus. This allows for more intuitive orientation of the ring, and parachuting of the ring down to the annulus without reorientation. In the embodiment depicted in FIG. 6, the longitudinal axis 67 of the post 18 is positioned at an angle 66 from a vertical plane 68 normal to the datum plane 70 of the ring 14. In the particular embodiment depicted, the angle is approximately 11 degrees, although other angles are also within the scope of the invention. For example, angles between 10 and 15 degrees may be useful for ring holders. Other angles can also be selected, depending on the particular application.

The optimal angle may not be constant for every patient or surgeon. For example, different patients often have different physical characteristics of their respective mitral valves. Also, different surgeons may use slightly different approaches to the mitral valve, or may have certain preferences with respect to viewing angles, etc.

Figures 7, 8, 9:
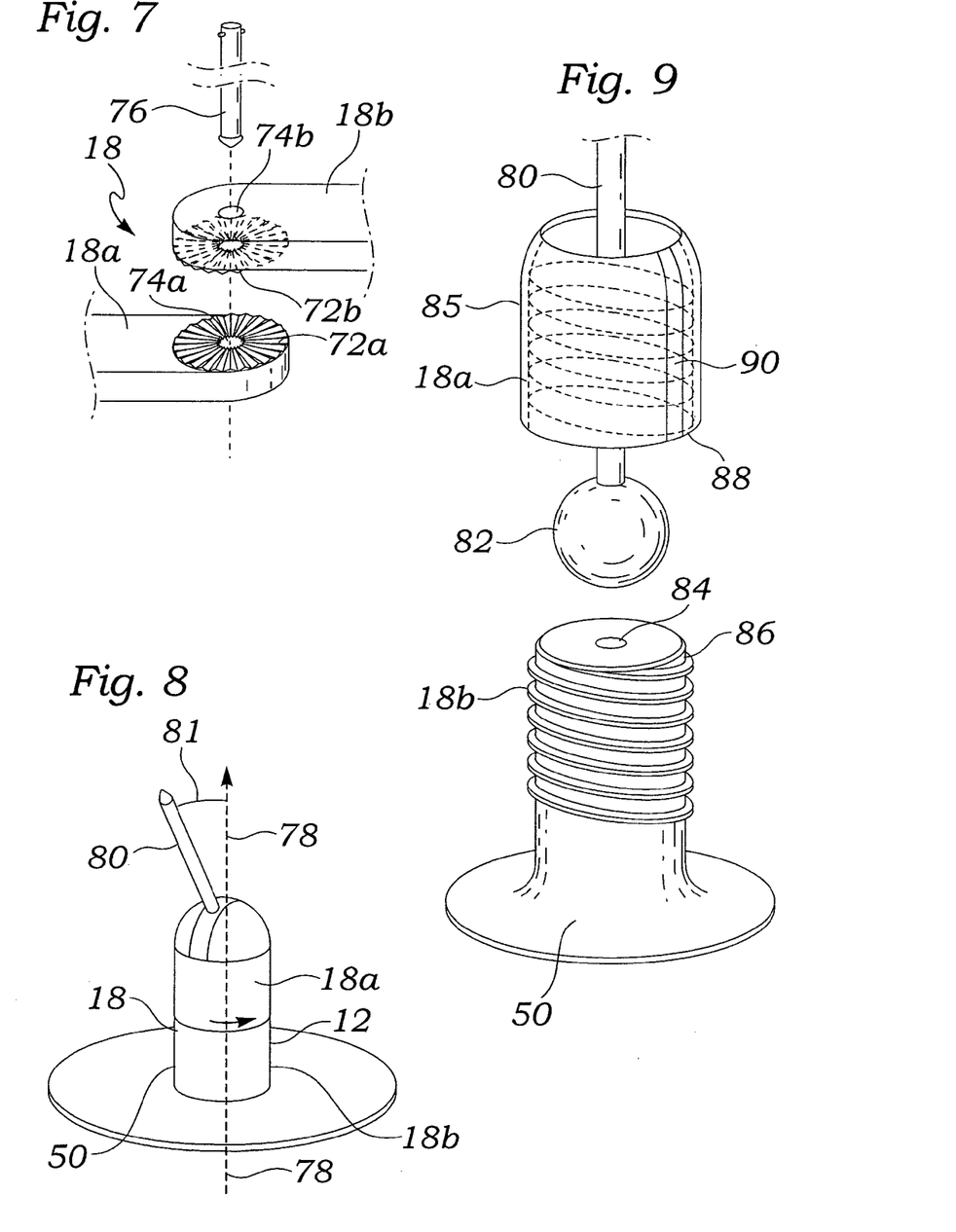
FIG. 7 is a perspective view of a portion of a ring holder according to an embodiment of the invention.
FIG. 8 is a perspective view of a portion of a ring holder according to an embodiment of the invention.
FIG. 9 is an exploded perspective view of the portion of the ring holder depicted in FIG. 8.

A single-pivot structure can be helpful in adjusting the angle as desired. As depicted in FIG. 7, a holder post 18 having a proximal portion 18a and a distal portion 18b, with the distal portion 18b secured to the central base portion (not shown) of the holder 12. The proximal portion 18a can be pivoted with respect to the distal portion 18b, which permits a user to adjust the holder post angle to achieve the optimal angle for the specific application. The proximal portion 18a has a toothed fitting 72a configured to interlock with a corresponding toothed fitting 72b on the distal portion 18b. Each toothed fitting has a corresponding pin hole 74a, 74b at its center. A releasable compression pin 76 is configured to pass through the pin holes 74a, 74b. With the compression pin 76 tightened in place, it holds the toothed portions 72a, 72b in engagement, maintaining a fixed angle between the proximal portion 18a and distal portion 18b of the post 18. With the compression pin 76 loosened, the user can adjust the angle between the proximal portion 18a and distal portion 18b of the post 18, and then lock the pin 76 into its tightened configuration in order to fix the proximal portion 18a and distal portion 18b at the desired angle.

In another embodiment of the invention, the holder may include the ability to change the rotational position of part of the holder with respect to the central base portion. This may be in addition to the ability to adjust the angle of the holder post. In the embodiment of FIGS. 8 and 9, the post 12 includes a distal portion 18b fixed to the central base portion 50. A post proximal portion 18a is rotationally secured to the distal portion, so that the proximal portion 18a can rotate about the holder longitudinal axis 78. The rotation of the proximal portion 18a can be controlled by conventional methods, such as having a releasable lock (not shown) that selectively prevents rotation.

To permit adjustment of the angle between the ring datum plane and a portion of the post, the post 18 has an additional proximal structure 80 that can be adjusted in angle 81 with respect to the ring datum plane and holder longitudinal axis 78. The additional proximal structure 80 can be releasably and/or adjustably secured to the rest of the post 18 so that the angle 81 can be modified as the user desires. Conventional structures can be used to accomplish this feature.

In the embodiment of FIGS. 8-9, a rotational ball and retainer structure is used. The additional proximal structure 80 includes a ball 82 configured to cooperate with a corresponding recess 84 in the post distal portion 18b. An adjustable housing 85, which also forms the post proximal portion 18a, is configured to hold the ball 82 against the recess 84. The adjustable housing 85 includes a slit 90, which facilitates removal of the adjustable housing from the additional proximal structure 80 and also permits the additional proximal structure 80 to be rotated to relatively extreme angles. The adjustable housing 85 can be screwed onto the post distal portion 18b via corresponding threading 86, 88 on the post distal portion 18b and in the adjustable housing 85. By loosening (i.e., unscrewing) the adjustable housing 85 from the post distal portion 18b, a user will loosen the additional proximal structure 80 and permit adjustment of the angle and rotation thereof. Once the desired angle and rotation are achieved, the user can tighten the adjustable housing 85 onto the post distal portion 18b, which will secure the additional proximal structure 18 at the desired angle and rotation.

Another embodiment involves a similar ball and housing structure to that depicted in FIGS. 8 and 9, but with the ball structure positioned on the post and the adjustable housing on the additional proximal structure. In such an embodiment, the ball is attached to the holder and the housing is lengthened and turned upside down to become part of the handle and/or additional proximal structure. There is an additional structure that threads inside of the housing. At the distal end of this structure there is mechanism that allows a user to thread the structure into or out of the housing and thus move the structure relative to the housing. At the other end of the structure there is a recess that conforms to the shape of the ball. With this embodiment, a user can tighten or loosen the housing by rotating the handle and/or adjusting additional proximal structure(s). The additional proximal structure could be located at the proximal end of the handle, and could include angle adjustment and/or rotation adjustment controls. This permits a surgeon to make an adjustment to angle and rotation at a distance (i.e. by turning a control knob at the proximal end of the handle).

In minimally invasive surgery (MIS) approaches to the mitral valve, the annuloplasty ring is typically passed through a relatively small port into the chest. This can be complicated by some holders, which can interfere with introducing the annuloplasty ring into the chest. Depending on the particular application, the current invention's feature of adjusting the holder post angle and/or rotational position can also allow easier passage of the ring and holder into the chest cavity. Such adjustment can occur before and/or during the surgical procedure. For example, a surgeon may select an initial rotation and angle during initial surgical procedures, then select another rotation and/or angle for introduction of the ring and holder through the chest wall, and then select still another rotation and/or angle for final placement of the ring.

Figure 10A:
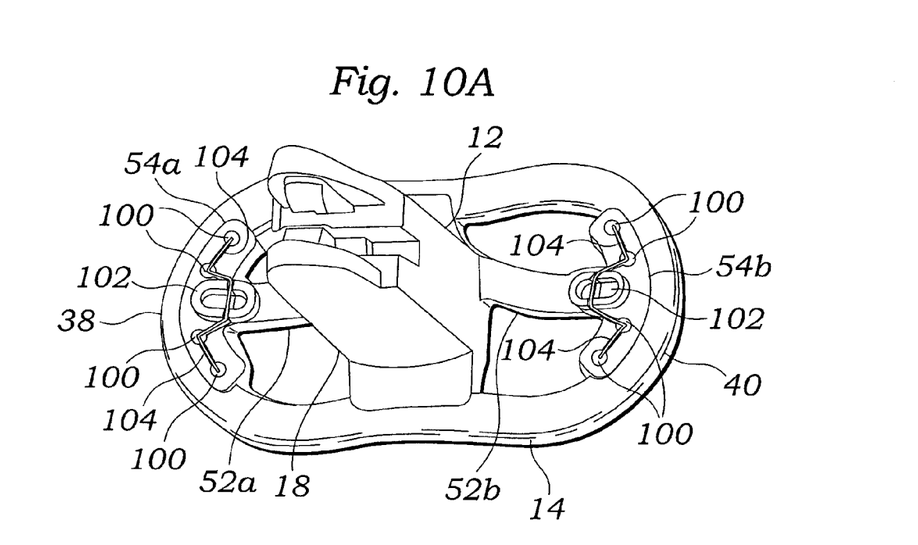
FIG. 10A is a perspective view of ring and ring holder according to an embodiment of the invention.

FIG. 10A which depicts a holder 12 and ring 14 combination in accordance with an embodiment of the invention. The arrangement of relatively narrow radial arms 52a, 52b and relatively narrow and short arcuate outer sections 54a, 54b enhances visibility, leaving open a large portion of the area encompassed by the ring 14. Suture holes 100 are positioned at distal ends 54a, 54b of the arms 52a, 52b, with corresponding suture wells 102 positioned on the arms 52a, 52b. In the embodiment of FIG. 10, the suture wells 102 are positioned on the arms 52a, 52b to correspond with the sides 38, 40 of the ring 14. Restraining sutures 104 pass through the suture holes 100 and suture wells 102. The suture wells 102 are configured to provide an easily accessible location for the surgeon to cut the suture 104 passing therethrough. Due to the structure of the particular ring 14, which is relatively short along its minor axis when compared to its length along the major axis, the areas of the ring 14 and holder 12 corresponding to the ring sides 38, 40 are generally the areas which are most easily accessible to the surgeon during an implantation procedure. By positioning the suture wells 104 at these areas (which are furthest away from the holder central portion and post), the invention facilitates the ease by which the surgeon can sever the restraining sutures in order to release the ring 14 from the holder 12.

Figure 10B:
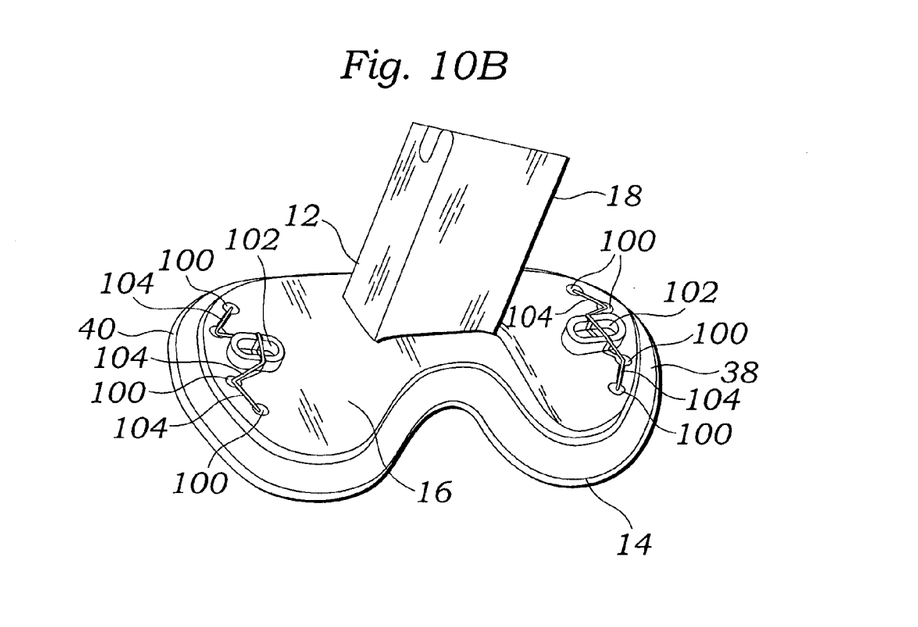
FIG. 10B is a perspective view of ring and ring holder according to an embodiment of the invention.

A similar embodiment is depicted in FIG. 10B, which has a holder 12 and ring 14. The holder 12 of FIG. 10B has a generally solid lower template portion 16 (instead of the arms 52a, 52b depicted in FIG. 10A). In the embodiment of FIG. 10B, the suture wells 102 are positioned on the lower template portion 16 to correspond with the sides 38, 40 of the ring 14. Restraining sutures 104 pass through the suture holes 100 and suture wells 102. The suture wells 102 are configured to provide an easily accessible location for the surgeon to cut the suture 104 passing therethrough.

In the embodiments depicted in FIGS. 10A and 10B, there are only two suture wells. However, other numbers of suture wells, from one (1) and up, are within the scope of the invention, depending on the particular number of sutures. As a general rule, fewer sutures and corresponding suture wells leads to greater ease in cutting the sutures. By limiting the number of sutures and/or suture wells, and by positioning the suture wells at those areas that are easiest to access, the invention facilitates the ease by which the surgeon can sever the restraining sutures.

Figure 11:
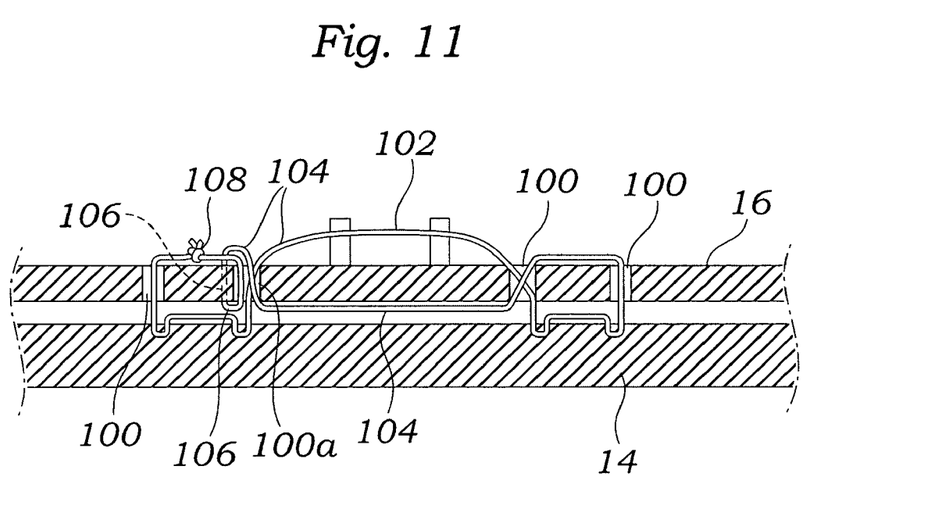
FIG. 11 is a side view, in cross-section, of a portion of a ring and ring holder according to an embodiment of the invention.

Another feature of the invention is an improved suture routing approach. The approach is depicted in FIG. 11, wherein a single piece of suture line 104 passes in the depicted pattern through the various suture holes 100, across the suture well 102, and through portions of the ring 14. Note that the suture could pass through portions of the ring, as depicted in FIG. 11, and/or could pass around portions of the ring. For one suture hole 100a, the suture passes through the suture hole 100a, then forms a loop 106 around a flange or other edge of the holder lower template portion 16, and then passes back through the suture hole 100a (in the same direction that it passed through previously), thereby providing resistance to the suture slipping with respect to the holder lower template portion 16. The suture 104 is tied to itself. In the embodiment depicted, a double square knot 108 is used to secure the suture to itself. Note that other knots are also within the scope of the invention. The described suture routing provides wider attachment points for greater stability of the ring on the holder, without increasing the likelihood of a high suture pull-out resistance.

While the invention has been described with reference to particular embodiments, it will be understood that various changes and additional variations may be made and equivalents may be substituted for elements thereof without departing from the scope of the invention or the inventive concept thereof. For example, while the invention is specifically discussed in application with mitral valve repair, it has applicability in other areas where it is desired to repair valves and similar structures. In addition, many modifications may be made to adapt a particular situation or material to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. An annuloplasty ring and holder assembly combination, comprising:
   an annuloplasty ring, the annuloplasty ring having a minor axis, a major axis, and a maximum height, the major axis being greater than the minor axis such that the ring elongated along the major axis; and
   a ring holder, the holder comprising:
   a base structure;
   a first knob extending from the base structure to a first knob inner edge of the annuloplasty ring, the first knob extending in a first knob direction generally along the minor axis of the annuloplasty ring; and a second knob extending from the base structure to a second knob inner edge of the annuloplasty ring, the second knob extending in a second knob direction generally along the minor axis of the annuloplasty ring, wherein the second knob direction is generally opposite to the first knob direction;

first and second radial arms generally extending in opposite directions from the base structure to first and second radial arm inner edges of the annuloplasty ring, the first and second radial arms terminating in first and second ring securing portions;

first and second securing sutures respectively connecting the annuloplasty ring to the first and second ring securing portions, wherein the first and second knobs contact the annuloplasty ring but are not secured thereto, the ring holder thus contacting the annuloplasty ring inner edge at four separate locations and being secured thereto at only two of those locations.

2. The combination of claim 1, wherein the base structure has a base width and a base height and wherein the first knob has a first knob maximum width less than the base width.

3. The combination of claim 2, wherein the base structure has a base width and a base height, and wherein the second knob has a second knob maximum width less than the base width.

4. The combination of claim 1, wherein the first knob has a first knob distal width less than the base width.

5. The combination of claim 4, wherein the second knob has a second knob distal width less than the base width.

6. The combination of claim 1, wherein the first knob has a first knob minimum distal width less than the base width.

7. The combination of claim 6, wherein the second knob has a second knob distal width less than the base width.

8. The combination of claim 1, wherein the first and second radial arms extend along the ring major axis, and the first and second ring securing portions comprise arcuate segments that respectively conform to the radial arm inner edges of the annuloplasty ring.

9. An annuloplasty ring and holder assembly combination, comprising:

an annuloplasty ring, the annuloplasty ring having a minor axis and a major axis;

a ring holder comprising a lower template structure defined by a base structure and two radially extending arms generally extending in opposite directions from the base structure to first and second radial an-n inner edges of the annuloplasty ring, the first and second radial arms terminating in first and second ring securing portions, wherein the ring holder does not contact the annuloplasty ring on both sides of the first and second ring securing portions such that they are spaced from each other around the annuloplasty ring, wherein each of the first and second ring securing portions comprises a suture cutting well and four (4) adjoining suture holes; and a suture line, the suture line passing through each of the four (4) adjoining suture boles, across the suture cuffing well, and within or around at least a portion of the annuloplasty ring;

and first and second knobs respectively extending generally along the minor axis from the base structure to first and second knob inner edges of the annuloplasty ring, the ring holder thus contacting the annuloplasty ring inner edge at four separate locations and being secured thereto at only two of those locations.

\* \* \* \* \*